US00PP29566P2

(12) United States Plant Patent
O'Connell

(10) Patent No.: US PP29,566 P2
(45) Date of Patent: Jul. 31, 2018

(54) ***AEONIUM* 'TENERIFE ROSE'**

(50) Latin Name: *Aeonium hybrida*
Varietal Denomination: Tenerife Rose

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/731,161

(22) Filed: Apr. 26, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Aeonium* cultivar named 'Tenerife Rose' is disclosed, characterized by green foliage distinctively margined with a dark bronze color. Offsets are formed in distinctive vertical tiers, producing a more columnar plant. Plants are robust and grow quickly., while maintaining an attractive compact habit. *Aeonium* is, typically produced as a container plant for the patio or for landscape use.

1 Drawing Sheet

Latin name of the genus and species: *Aeonium hybrida.*
Variety denomination: 'TENERIFE ROSE'.

BACKGROUND OF THE INVENTION

The new cultivar, *Aeonium* 'Tenerife Rose', was found by the inventor, Renee O'Connell, as the result of a crossing made January 2012 as part of a planned breeding program. The seed parent variety is the unpatented proprietary variety referred to as *Aeonium hybrida* 'Cat 07'. The pollen parent is the unpatented variety *Aeonium hybrida* 'Bordeaux'. *Aeonium* 'Tenerife Rose' was selected by the inventor, Renee O Connell, in April of 2013 from a group of seedlings resulting from the 2013 crossing, at a commercial greenhouse in Vista. Calif.

Asexual reproduction of the new cultivar 'Tenerife Rose' was first performed in Vista, Calif., at a commercial greenhouse, by vegetative off-sets in October of 2013. 'Tenerife Rose' has since produced multiple generations and has shown that the unique features of this cultivar are stable and reproduced true to type.

SUMMARY OF THE INVENTION

The cultivar 'TENERIFE ROSE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TENERIFE ROSE' These characteristics in combination distinguish 'TENERIFE ROSE' as a new and distinct *Aeonium* cultivar:

1. Fast, robust growth, more so than many other *Aeonium* species and cultivars.
2. *Aeonium* 'Tenerife Rose' freely offsets, producing tiers of offsets to quickly form a desirable specimen for the landscape 3. *Aeonium* 'Tenerife Rose', rather than clustering laterally as do many comparable *Aeoniums*, produces tiers of offsets more vertically, continuing to produce offsets towards the apical meristem of the plant.
4. *Aeonium* 'Tenerife Rose', as a result of the habit of producing more of a columnar morphology, is better suited as a centerpiece in a garden or dish garden planting, than many other comparable *Aeoniums.*

COMPARISON TO PARENTS

Plants of the new cultivar 'TENERIFE ROSE' are similar to plants of the seed parent in most horticultural characteristics, however, plants of the new cultivar 'TENERIFE ROSE' differ in the following;

1. *Aeonium* 'Tenerife Rose' exhibits a more columnar morphology than the seed parent.
2. *Aeonium* 'Tenerife Rose' produces rosettes of leaves of a medium green, distinctively outlined with a darker color, whereas the leaves of *Aeonium* 'Cat 07' are a dark brownish color.
3. *Aeonium* 'Tenerife Rose' exhibits offsets towards the apical meristem of the plant, whereas *Aeonium* 'Cat 07' produces offsets mostly approximately halfway up the plant, and does not continue to produce offsets towards the apical meristem.
4. *Aeonium* 'Tenerife Rose' grows faster than *Aeonium* 'Cat 07'.
5. *Aeonium* 'Tenerife Rose' produces more offsets than does *Aeonium* 'Cat 07'.

Plants of the new cultivar 'TENERIFE ROSE' are similar to plants of the pollen parent in most horticultural characteristics, however, plants of the new cultivar 'TENERIFE ROSE' differ in the following;

1. *Aeonium* 'Tenerife' Rose' produces rosettes that are a slightly darker green than those of *Aeonium* 'Bordeaux'.

2. *Aeonium* 'Bordeaux' offsets freely, but tends to produce the offsets laterally, whereas *Aeonium* 'Tenerife Rose' produces the offsets more vertically.
3. *Aeonium* 'Tenerife Rose' exhibits a distinctive darker leaf margin, whereas *Aeonium* 'Bordeaux' displays a more subtle difference between the margin/blush and the green color.
4. *Aeonium* 'Bordeaux' grows to approximately 12" in height, whereas *Aeonium* hybrid 'Tenerife Rose' grows to approximately 18" in height.

COMMERCIAL COMPARISON

Plants of the new cultivar 'TENERIFE ROSE' are comparable to the unpatented, commercial variety *Aeonium* 'Escondido'. The two *Aeonium* varieties are similar in most horticultural characteristics; however, the new variety 'TENERIFE ROSE' differs in the following:

1. *Aeonium* 'Tenerife Rose' grows more upright than does *Aeonium* 'Escondido', producing a specimen that is taller in height.
2. *Aeonium* 'Escondido' produces offsets laterally, whereas *Aeonium* 'Tenerife Rose' continues to produce offsets near the apical meristem, resultant in a more vertical growth of the offsets in relation to the principal plant.
3. *Aeonium* 'Tenerife Rose' forms rosettes of green leaves, with distinctive darker margins and darker overall blush in strong light, whereas *Aeonium* 'Escondido' produces rosettes of green leaves with a ruddy blush and margins.

Plants of the new cultivar 'TENERIFE ROSE' can also be comparable to the unpatented commercial variety *Aeonium* 'Party Platter'. The two *Aeonium* varieties are similar in most horticultural characteristics; however, the new variety 'TENERIFE ROSE' differs in the following:

1. *Aeonium* 'Tenerife Rose' begins to offset when the plant is only 8" or so in height, whereas *Aeonium* 'Zwartkop' does not offset until it is taller.
2. *Aeonium* 'Tenerife Rose' produces offsets freely, often in multiple tiers that create an aesthetically appealing cluster, whereas *Aeonium* 'Zwartkop' produces less offsets, and does not produce the offsets in multiple tiers, resultant in a lankier plant that does not display the pleasing appearance of a "full cluster".
3. *Aeonium* 'Tenerife Rose' forms rosettes of medium green leaves with a distinct darker margin and a darker blush in strong light, whereas *Aeonium* 'Zwartkop' forms rosettes of dark, nearly black leaves.
4. *Aeonium* 'Tenerife Rose' can fill a production pot with an attractive cluster with one cut in several months, whereas it is necessary to plant multiple plantlets of *Aeonium* 'Zwartkop' in the production pot to give the impression of "branching", resulting in higher production costs.

BRIEF DESCRIPTION OF THE PHOTOGRAPH

The accompanying photograph illustrates in full color a typical of plant of *Aeonium* 'Tenerife Rose' grown in a shadehouse in Vista, Calif. at a light intensity of approximately 2500 to 3500 fc.

Age of the plant photographed is approximately 10 months from a rooted plantlet. The photograph was taken using conventional techniques and although colors may appear different from actual colors due to light reflectance it is as accurate as possible by conventional photographic techniques. All photographs provided by the breeder.

DETAILED BOTANICAL DESCRIPTION

In the following description, color references are made to The Royal Horticultural Society Colour Chart, 2007, except where general terms of ordinary dictionary significance are used. The following observations and measurements describe 'Tenerife Rose' plants in a commercial shade house in Vista, Calif. Temperatures ranged from approximately 6° C. to 35° C. night and day. No artificial light, photoperiodic treatments or chemical treatments were given to the plants. Natural light conditions were approximately 4000 fc of light. Measurements and numerical values represent averages of typical plant types.

Botanical classification: *Aeonium hybrida* 'Tenerife Rose'.

PROPAGATION

Type of propagation typically used: Vegetative offsets.

Time to initiate roots: About 18 days at approximately 24° C.

Root description: Fibrous, brown, not accurately measured with a color chart.

PLANT

Age of plant described: Approximately 4 months.

Container size of the plant described: 1 gallon.

Growth habit: Upright, caulescent, with a somewhat loose terminal rosette, very freely offsetting.

Height: Approximately 27 cm to top of highest leaf.

Plant spread: 32 cm.

Growth rate: Moderately fast.

Branching characteristics: Freely offsetting.

Rosettes per plant: Average range 10 to 16.

FOLIAGE

Leaf:

*Arrangement.*—Rosulate.

*Average length.*—Outer rosette mature leaf approximately 12 cm. Inner rosette mature leaf approximately 7.0 cm.

*Average width.*—3.0 to 4.2 cm.

*Width at base.*—1.2 cm.

*Shape of blade.*—Spatulate.

*Apex.*—Mucronate. Immature aspices rounded, mature foliage aspices more angular and sloped than rounded.

*Base.*—Cuneate.

*Margin.*—Finely ciliate.

*Texture of top surface.*—Glabrous.

*Texture of bottom surface.*—Glabrous.

*Quantity of leaves per rosette.*—Average range 40 to 60.

*Color.*—Young foliage upper side: Base Yellow-Green 144D. Mid-section near Green 137C, uppermost section Green 137A. Apical margin 187A. Young foliage, under side: Small basal section near Yellow-Green 144D. Mid-section near Green 137B, large uppermost section Green 137A. Apical margin 187B. Mature foliage upper side: Base Yellow-Green 144C. Mid-section Green 137C. Large uppermost section Green 137B. Apical margin 187A. Mature foliage, under side: Base Yellow-Green 144C. Mid-section Green 137D. Large uppermost section Green 137C. Apical margin 187A.

*Venation*.—There is no visual appearance of venation.

FLOWER

Flowering not observed to date.

REPRODUCTIVE ORGANS

Flowering not observed to date.

OTHER CHARACTERISTICS

Fruits and seeds: Plant has not flowered or produced fruits and seeds to date.

Temperature tolerance: Tolerates temperatures from approximately −2 degrees C. to 40 degrees C.

Disease/pest resistance: Displays the same disease and pest resistance of any other comparable *Aeonium*.

Drought tolerance: Tolerates at least 3 weeks of high temperatures without supplemental water, showing no serious damage to plant.

What is claimed is:

1. A new and distinct cultivar of *Aeonium* plant named 'TENERIFE ROSE' as herein illustrated and described.

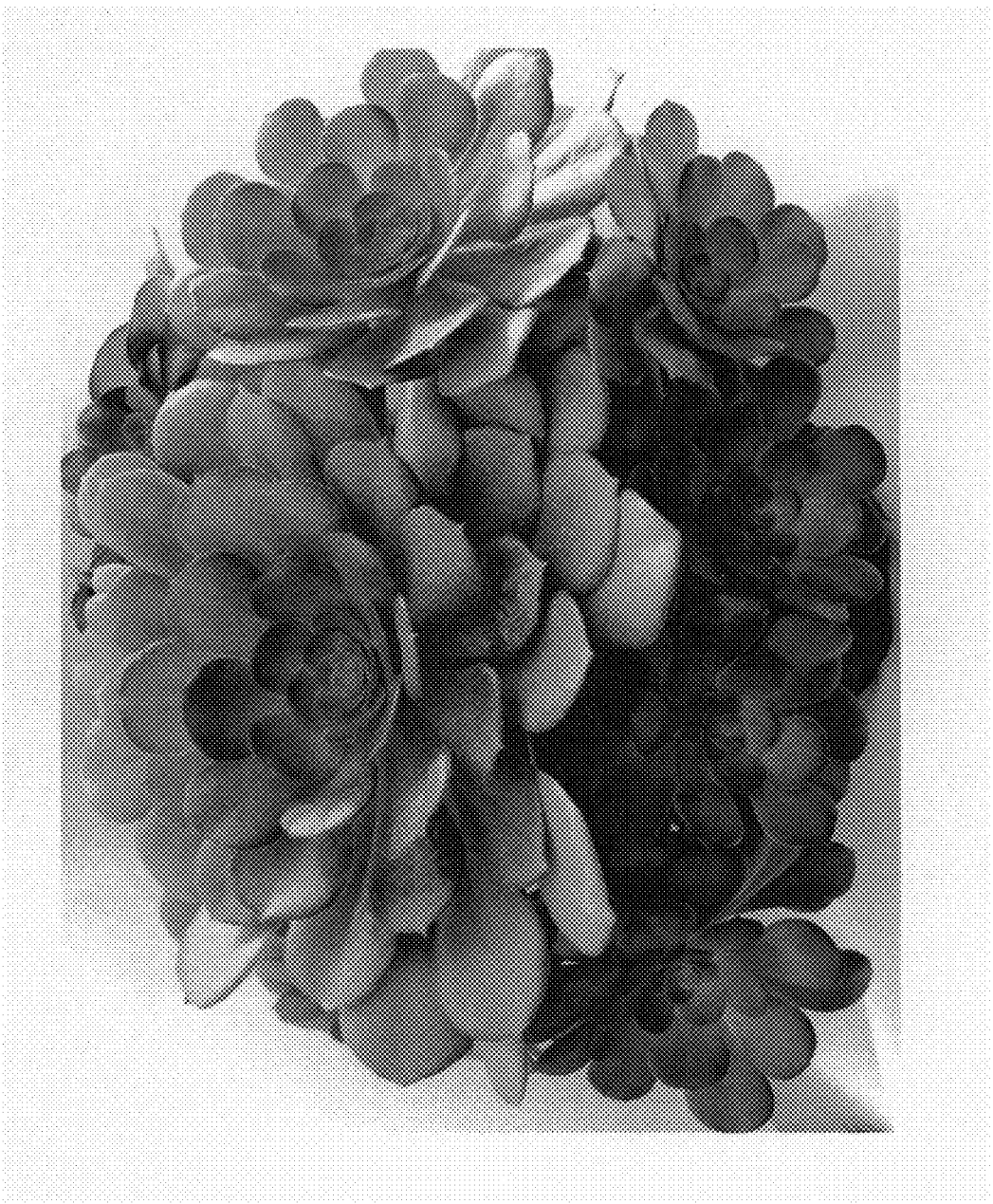

* * * * *